United States Patent [19]

Rajagopolan et al.

[11] Patent Number: 5,376,358
[45] Date of Patent: Dec. 27, 1994

[54] MAGNETIC RESONANCE IMAGING AGENTS

[75] Inventors: Raghavan Rajagopalan, Maryland Heights; Muthunadar P. Periasamy, Creve Coeur, both of Mo.

[73] Assignee: Mallinckrodt Medical, Inc., St. Louis, Mo.

[21] Appl. No.: 631,508

[22] Filed: Dec. 21, 1990

Related U.S. Application Data

[60] Division of Ser. No. 402,623, Sep. 5, 1989, Pat. No. 5,011,925, which is a continuation-in-part of Ser. No. 321,265, Mar. 9, 1989, abandoned.

[51] Int. Cl.$^5$ .............................................. A61K 49/00
[52] U.S. Cl. ................................ 424/9; 340/465; 514/185; 514/318; 514/184; 534/15; 534/16
[58] Field of Search ............ 424/9; 514/185, 184–318; 534/15, 16; 540/465

[56] References Cited

U.S. PATENT DOCUMENTS

| | | | |
|---|---|---|---|
| 3,507,892 | 4/1970 | Bersworth | 564/155 |
| 3,787,482 | 1/1974 | Bersworth | 564/155 |
| 3,859,337 | 1/1975 | Herz et al. | 564/155 |
| 4,001,212 | 1/1977 | Richman et al. | 540/465 |
| 4,174,319 | 1/1977 | Kobuke | 540/465 |
| 4,174,428 | 1/1977 | Tabushi et al. | 540/465 |
| 4,352,751 | 10/1982 | Wieder et al. | 552/540 |
| 4,432,907 | 2/1984 | Wieder et al. | 552/540 |
| 4,639,365 | 1/1987 | Sherry | 534/15 |
| 4,647,447 | 3/1987 | Gries et al. | 424/9 |
| 4,678,667 | 7/1987 | Meares et al. | 540/465 |
| 4,687,658 | 8/1987 | Quay | 424/9 |
| 4,687,659 | 8/1987 | Quay | 424/9 |
| 4,826,673 | 5/1989 | Dean et al. | 424/9 |
| 4,859,451 | 8/1989 | Quay et al. | 424/9 |
| 4,885,363 | 12/1989 | Tweedle et al. | 540/465 |
| 4,889,931 | 12/1989 | Rocklage et al. | 424/9 |
| 4,965,211 | 10/1990 | Wieder et al. | 552/540 |

FOREIGN PATENT DOCUMENTS

| | | | |
|---|---|---|---|
| 7899587 | 9/1987 | Australia | 424/9 |
| 1242643 | 12/1983 | Canada | 424/9 |
| 263059 | 9/1987 | European Pat. Off. | 424/9 |
| 250358 | 12/1987 | European Pat. Off. | 424/9 |
| 45083 | 1/1966 | German Dem. Rep. | 564/155 |
| 3401052 | 7/1984 | Germany | 424/9 |
| 3324235 | 1/1985 | Germany | 424/9 |
| 3324236 | 1/1985 | Germany | 424/9 |
| 2181428 | 1/1989 | United Kingdom | 424/9 |

OTHER PUBLICATIONS

Lauffer, Chemical Reviews 87, 1987 901–927.
Cacheris, et al Inorganic Chemistry 1987 25, 959–960.
A–Z of Clinical Chemistry, A Guide for the Trainee, MTP Press Limited, Lancaster, England (1980) p. 126.
Organic Chemistry, 4th Ed. Allyn & Bacon, Inc., Boston (1983) p. 1056.
2 Patent Practice 10-10 (1989).
Grant and Hackh's Chemical Dictionary, Grant & Grant, McGraw-Hill Book Company New York (1987) pp. 14, 31, 53, 559.
Lauterbur, Nature, 242:190-1 (1973), Image Formation by Induced Local Interactions: Examples Employing . .

(List continued on next page.)

Primary Examiner—Robert T. Bond
Assistant Examiner—E. C. Ward
Attorney, Agent, or Firm—Rothwell, Figg, Ernst & Kurz

[57] ABSTRACT

Novel magnetic resonance imaging agents comprise complexes of paramagnetic ions with aminoalkylamide derivatives of diethylenetriaminepentaacetic acid ("DTPA") or ethylenediaminetetraacetic acid ("EDTA") or other polyaminocarboxylic or cyclic polyaminocarboxylic chelating agents. These novel imaging agents are characterized by excellent NMR image-contrasting properties and by high solubilities in physiological solutions.

A novel method of performing an NMR diagnostic procedure involves administering to a warm-blooded animal an effective amount of a complex as described above and then exposing the warm-blooded animal to an NMR imaging procedure, thereby imaging at least a portion of the body of the warm-blooded animal.

31 Claims, No Drawings

OTHER PUBLICATIONS

Damadian, *Science*, 171:1151-3 (1971), Tumor Detection by Nuclear Magnetic Resonance.

Weimann et al., *AJR*, 142:619:624 (1984) Characteristics of Gadolinium DPTA Complex.

Weimann et al., *AJR*, 142:625-630 (1984), Contrast Enhanced NMR Imaging: Animal Studies . . . .

Hornig et al., Van Nostrand Chemist's Dictionary, p. 44 (1962).

Aisen, Society of Magnetic Resonance Imaging, Eigth Annual Meeting Program & Abstracts, p. 46 (1990).

MAGNETIC RESONANCE IMAGING AGENTS

This is a division of application Ser. No. 07/402,623, filed Sep. 5, 1989, now U.S. Pat. No. 5,011,925 granted Apr. 22, 1991. Application Ser. No. 07/402,623 is a continuation-in-part of application Ser. No. 321,265, filed Mar. 9, 1989, now abandoned.

BACKGROUND OF THE INVENTION

This invention relates to nuclear magnetic resonance (NMR) imaging and, more particularly, to methods and compositions for enhancing NMR imaging.

The recently developed technique of NMR imaging encompasses the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. As currently used, the images produced constitute a map of the proton density distribution and/or their relaxation times in organs and tissues. The technique of NMR imaging is advantageously non-invasive as it avoids the use of ionizing radiation.

While the phenomenon of NMR was discovered in 1945, it is only relatively recently that it has found application as a means of mapping the internal structure of the body as a result of the original suggestion of Lauterbur (Nature, 242, 190-191 (1973)). The fundamental lack of any known hazard associated with the level of the magnetic and radio-frequency fields that are employed renders it possible to make repeated scans on vulnerable individuals. In additional to standard scan planes (axial, coronal, and sagittal), oblique scan planes can also be selected.

In an NMR experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla ($10^4$ gauss)) align in the direction of the field. In the case of protons, these nuclei precess at a frequency, f, of 42.6 MHz at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In NMR imaging, scanning planes and slice thicknesses can be selected. This selection permits high quality transverse, coronal and sagittal images to be obtained directly. The absence of any moving parts in NMR imaging equipment promotes a high reliability. It is believed that NMR imaging has a greater potential than CT for the selective examination of tissue characteristics in view of the fact that in CT, x-ray attenuation coefficients alone determine image contrast, whereas at least five separate variables ($T_1$, $T_2$, proton density, pulse sequence and flow) may contribute to the NMR signal. For example, it has been shown (Damadian, Science, 171, 1151 (1971)) that the values of the $T_1$ and $T_2$ relaxation in tissues are generally longer by about a factor of 2 in excised specimens of neoplastic tissue compared with the host tissue.

By reason of its sensitivity to subtle physicochemical differences between organs and/or tissues, it is believed that NMR may be capable of differentiating different tissue types and in detecting diseases which induce physicochemical changes that may not be detected by x-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei (e.g., viscosity, temperature, and the like). These two relaxation phenomena are essentially mechanisms whereby the initially imparted radio frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment within which it finds itself.

In general, paramagnetic divalent or trivalent ions of elements with an atomic number of 21 to 29, 42 to 44 and 58 to 70 have been found effective as NMR image contrasting agents. Suitable such ions include chromium (III), manganese (II), manganese (III), iron (III), iron (II), cobalt (II), nickel (II), copper (II), praseodymium (III), neodymium (III), samarium (III) and ytterbium (III). Because of their very strong magnetic moments, gadolinium (III), terbium (III), dysprosium (III), holmium (III) and erbium (III) are preferred. Gadolinium (III) ions have been particularly preferred as NMR image contrasting agents.

Typically, the divalent and trivalent paramagnetic ions have been administered in the form of complexes with organic complexing agents. Such complexes provide the paramagnetic ions in a soluble, non-toxic form, and facilitate their rapid clearance from the body following the imaging procedure. Gries et al., U.S. Pat. No. 4,647,447, disclose complexes of various paramagnetic ions with conventional aminocarboxylic acid complexing agents. A preferred complex disclosed by Gries et al. is the complex of gadolinium (III) with diethylenetriaminepentaacetic acid ("DTPA"). This complex may be represented by the formula:

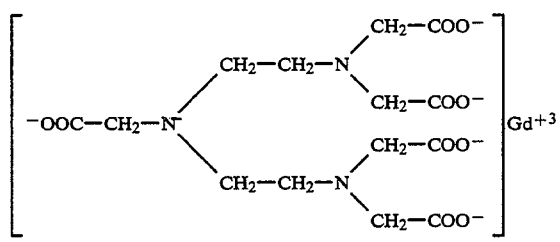

Paramagnetic ions, such as gadolinium (III), have been found to form strong complexes with DTPA. These complexes do not dissociate substantially in physiological aqueous fluids. The complexes have a net charge of −2, and generally are administered as soluble salts. Typical such salts are the sodium and N-methylglucamine salts.

The administration of ionizable salts is attended by certain disadvantages. These salts can raise the in vivo ion concentration and cause localized disturbances in osmolality, which in turn, can lead to edema and other undesirable reactions.

Efforts have been made to design non-ionic paramagnetic ion complexes. In general, this goal has been achieved by converting one or more of the free carboxylic acid groups of the complexing agent to neutral, non-ionizable groups. For example, S. C. Quay, in U.S. Pat. Nos. 4,687,658 and 4,687,659, discloses alkylester and alkylamide derivatives, respectively, of DTPA complexes. Similarly, published West German applications P 33 24 235.6 and P 33 24 236.4 disclose mono- and polyhydroxyalkylamide derivatives of DTPA and their use as complexing agents for paramagnetic ions. Published Australian Patent Application No. 78995/87 also describes amide complexing agents useful in NMR and x-ray procedures.

The nature of the derivative used to convert carboxylic acid groups to non-ionic groups can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al., AJR, 142, 679 (Mar. 1984) and Brasch et al., AJR, 142, 625 (Mar. 1984).

Thus, a need continues to exist for new and structurally diverse non-ionic complexes of paramagnetic ions for use as NMR imaging agents.

SUMMARY OF THE INVENTION

The present invention provides novel complexing agents and complexes of complexing agents with paramagnetic ions. The complexes are represented by either of the following formulae:

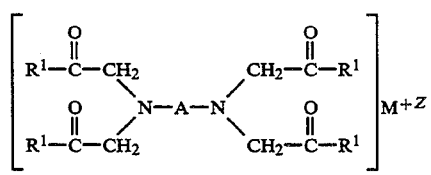

I.

wherein A is —CHR$^2$—CHR$^3$— or

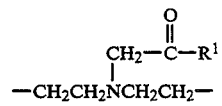

$M^{+Z}$ is a paramagnetic ion of an element with an atomic number of 21-29, 42-44 or 58-70, and a valence, Z, of +2 or +3; R$^1$ groups may be the same or different and are selected from the group consisting of —O$^-$ and

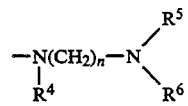

wherein R$^4$, R$^5$ and R$^6$ may be the same or different and are hydrogen, alkyl, hydroxy, alkoxy, mono- or polyhydroxyalkyl, alkoxyalkyl, aminoalkyl or acylaminoalkyl wherein the carbon-containing portions contain from 1 to about 6 carbon atoms or R$^5$ and R$^6$, together with the adjacent nitrogen, can form a heterocyclic ring of five, six or seven members wherein 0 to 1 members other than the nitrogen are

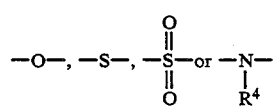

and which members are unsubstituted or substituted by hydroxy, alkyl, aryl, hydroxyalkyl, aminoalkyl, aminoaryl, alkylamino, or carbamoyl wherein the substituents contain from 1 to about 6 carbon atoms, n is between 1 and 6;

R$^2$ and R$^3$ may be the same or different and are hydrogen, alkyl having from 1 to about 6 carbon atoms, phenyl or benzyl or R$^2$ and R$^3$ together with the intervening carbon can form a hydrocarbon ring of 5, 6 or 7 members;

and wherein Z of the R$^1$ groups are —O$^-$ and the remainder of the R$^1$ groups are

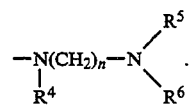

Alternatively, the complexes are represented by the following formula: II.

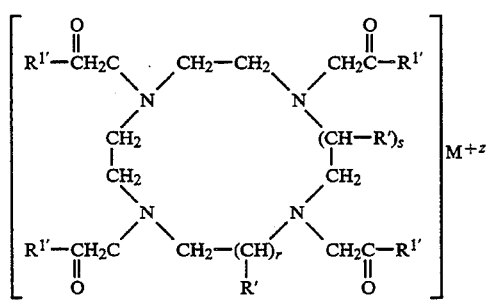

wherein $M^{+z}$ is a paramagnetic ion of an element with an atomic number of 21-29, 42-44 or 58-70, and a valence Z of +2 or +3, r and s are integers between 1 and 6 and can be the same or different, The R' groups can be the same or different and are selected from the group consisting of hydrogen, alkyl having from 1 to 6 carbon atoms and mono or polyhydroxyalkyl, the alkyl portion having from 1 to 6 carbon atoms, the $R^{1'}$ groups can be the same or different and are selected from the group consisting of $—O^-$ and

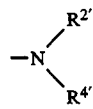

wherein $R^{2'}$ is selected from the group consisting of $(CH_2CH_2O)_p—R^{3'}$ and

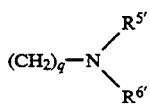

and $R^{4'}$ is selected from the group consisting of H, $R^{2'}$ and $R^{3'}$, wherein $R^{3'}$, $R^{5'}$ and $R^{6'}$ can be the same or different and are selected from the group consisting of hydrogen, alkyl, hydroxy, alkoxy, mono- or polyhydroxyalkyl, alkoxyalkyl, aminoalkyl or acylaminoalkyl, wherein the carbon-containing portions contain from 1 to about 6 carbon atoms or $R^{5'}$ and $R^{6'}$, together with the adjacent nitrogen, can form a heterocyclic ring of five, six or seven members wherein 0 to 1 members other than the nitrogen are $—O—$, $—S—$,

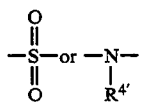

and which members are unsubstituted or substituted by hydroxy, alkyl, aryl, hydroxyalkyl, aminoalkyl, aminoaryl, alkylamino, or carbamoyl wherein the substituents contain from 1 to about 6 carbon atoms, p and q can be the same or different and represent integers between 1 and 6, and wherein z of the $R^{1'}$ groups are $—O^-$ and the remainder of the $R^{1'}$ groups are

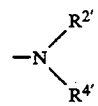

Also disclosed is a method of performing an NMR diagnostic procedure which involves administering to a warm-blooded animal an effective amount of one of the above-described complexes and then exposing the warm-blooded animal to an NMR imaging procedure, thereby imaging at least a portion of the body of the warm-blooded animal.

DETAILED DESCRIPTION OF THE INVENTION

The complexing agents employed in this invention are derivatives of well-known polyaminocarboxylic acid chelating agents, such as DTPA and ethylenediamine-tetraacetic acid ("EDTA") and cyclic polyaminocarboxylic acid chelating agents such as 1,4,7,10-tetraazacyclododecane N,N',N'',N'''-tetra acetic acid ("DOTA"). In one class of these derivatives, free carboxylic acid groups of the chelating agent (those not involved in bond formation with the paramagnetic ion) are converted to aminoalkylamide groups of the formula:

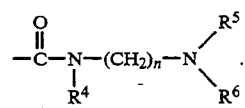

For example, if the polyaminocarboxylic acid chelating agent is DTPA, and the paramagnetic ion is trivalent, two of the carboxylic acid groups will be derivatized to the aminoalkylamide form. Likewise, if the paramagnetic ion is divalent, three of the carboxylic acid groups of DTPA or two of the carboxylic acid groups of EDTA will be derivatized to the aminoalkylamide form. When these complexing agents are reacted with a divalent or trivalent paramagnetic ion, the resulting complexes are substantially non-ionic as evidenced by very low electrical conductivity.

Examples of types of aminoalkylamide derivatives useful as complexes include those wherein the aminoalkylamide group is

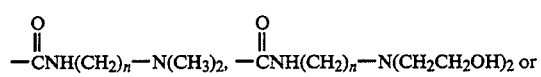

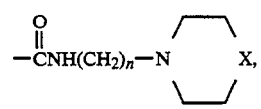

wherein X is O, S or N, unsubstituted or substituted. In a preferred embodiment, the aminoalkylamide group is a morpholinoalklylamide.

An alternative class of compounds encompassed by this invention, includes cyclic polyamino carboxylic acid chelating agents, such as DOTA and TRITA and represented by the general formula:

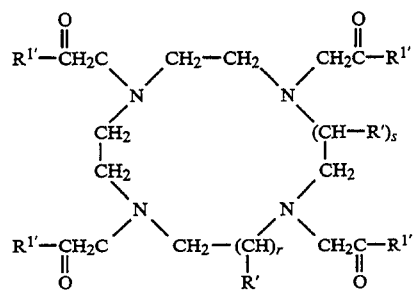

In these agents, free carboxylic acid groups are converted to

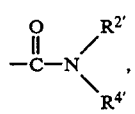

wherein $R^{2'}$ is either $(CH_2CH_2O)_p—R^{3'}$ or

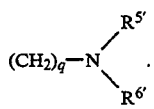

As with the first class of agents described above, if the paramagnetic ion is trivalent, one of the carboxylic acid groups will be derivatized to the aminoalkylamide form, and if the paramagnetic ion is divalent, two of the carboxylic acid groups will be derivatized.

Examples of types of derivatives useful as complexes include those wherein the amino alkylamide group is:

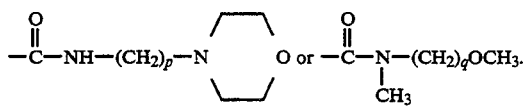

In a preferred embodiment, the aminoalkylamide group is morpholinoalkylamide.

The aminoalkylamide derivatives of the chelating agents may be prepared by conventional amide-forming reactions. In general, they are prepared by reacting a stoichiometric amount of an aminoalkylamine with a reactive derivative of the polyaminocarboxylic acid chelating agent or cyclic polyaminocarboxylic acid chelating agent under amide-forming conditions. Such reactive derivatives include, for example, anhydrides, mixed anhydrides and acid chlorides. To make complexing agents represented by formula I above, the aminoalkylamine has the general formula:

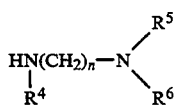

To make complexing agents represented by formula II above, the aminoalkylamide has the general formula:

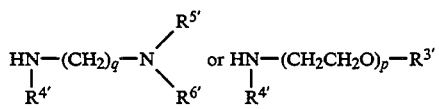

In one embodiment for making any of these complexing agents, the reactions are conducted in an organic solvent at an elevated temperature. Suitable solvents include those in which the reactants are sufficiently soluble and which are substantially unreactive with the reactants and products. Lower aliphatic ketones, ethers, esters, chlorinated hydrocarbons, benzene, toluene, xylene, lower aliphatic hydrocarbons, some lower aliphatic alcohols and the like may advantageously be used as reaction solvents. Examples of such solvents are isopropanol, acetone, methylethyl ketone, diethylketone, methyl acetate, ethyl acetate, chloroform, methylene chloride, dichloroethane, hexane, heptane, octane, decane, and the like. If an acid chloride derivative of the polyaminocarboxylic acid is used as the starting material, then the reaction solvent advantageously is one which does not contain reactive functional groups, such as hydroxyl groups, as these solvents can react with the acid chlorides, thus producing unwanted by-products.

The reaction temperature may vary widely, depending upon the starting materials employed, the nature of the reaction solvent and other reaction conditions. Such reaction temperatures may range, for example, from about 25° C. to about 80° C., preferably from about 25° C. to about 50° C.

Following reaction of the reactive polyaminocarboxylic acid derivative with the aminoalkylamide, any remaining anhydride or acid chloride groups can be hydrolyzed to the carboxylate groups by adding a stoichiometric excess of water to the reaction mixture and heating for a short time.

The resulting aminoalkylamide compound is recovered from the reaction mixture by conventional procedures. For example, the product may be precipitated by adding a precipitating solvent to the reaction mixture, and recovered by filtration or centrifugation.

The paramagnetic ion is combined with the aminoalkylamide compound under complex-forming conditions. In general, any of the paramagnetic ions referred to above can be employed in making the complexes of this invention. The complexes can conveniently be prepared by mixing a suitable oxide or salt of the paramagnetic ion with the complexing agent in aqueous solution. To assure complete complex formation, a slight stoichiometric excess of the complexing agent may be used. In addition, an elevated temperature, e.g., ranging from about 20° C. to about 100° C., preferably from about 40° C. to about 80° C., may be employed to insure complete complex formation. Generally, complete complex formation will occur within a period from a few minutes to a few hours after mixing. The complex may be recovered by precipitation using a precipitating solvent such as acetone, and further purified by crystallization or chromatography, if desired.

The novel complexes of this invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to 1.0M of a paramagnetic ion complex according to this invention. Preferred parenteral formulations have a concentration of paramagnetic ion complex of 0.1M to 0.5M. Such solutions also may contain pharmaceutically acceptable buffers and, optionally, electrolytes such as sodium chloride. The compositions advantageously can contain one or more physiologically acceptable, non-toxic cations in the form of a gluconate, chloride or other suitable organic or inorganic salt, including suitable soluble complexes with a chelant/ligand, to enhance safety. The chelant/ligand desirably is derived from DTPA or EDTA. Such ligands include the ligands set forth above used to complex the paramagnetic and or heavy metals to provide the complex formulations of this invention. Advantageously, the cation-ligand complex is provided in amounts ranging from about 0.1 mole % to about 15 mole % of the ligand-metal complex. Such physiologically acceptable, non-toxic cations include sodium ions, calcium ions, magnesium ions, copper ions, zinc ions and the like. Calcium ions are preferred. A typical single dosage formulation for parenteral administration has the following composition:

| | |
|---|---|
| Gadolinium DTPA-di(morpholinoethylamide) | 330 mg/ml |
| Calcium DTPA-tri(morpholinoethylamide) | 14 mg/ml |

| | |
|---|---|
| Distilled Water | q.s. to 1 ml |
| pH | 7.3 ± 0.1 |

Parenteral compositions can be injected directly or mixed with a large volume parenteral composition for systemic administration.

Formulations for enteral administration may vary widely, as is well-known in the art. In general, such formulations are liquids which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the particular paramagnetic ion complex employed, the organs or tissues which are the subject of the imaging procedure, the NMR imaging equipment being used, etc. In general, parenteral dosages will range from about 0.01 to about 1.0 mmol of paramagnetic ion complex per kg of patient body weight. Preferred parenteral dosages range from about 0.05 to about 0.5 mmol of paramagnetic ion complex per kg of patient body weight. Enteral dosages generally range from about 0.5 to about 100 mmol, preferably from about 1.0 to about 20 mmol of paramagnetic ion complex per kg of patient body weight.

The novel NMR image contrasting agents of this invention possess a unique combination of desirable features. The paramagnetic ion complexes exhibit an unexpectedly high solubility in physiological fluids, notwithstanding their substantially non-ionic character. This high solubility allows the preparation of concentrated solutions, thus minimizing the amount of fluid required to be administered. The non-ionic character of the complexes also reduces the osmolality of the diagnostic compositions, thus preventing undesired edema and other side effects.

As illustrated by the data presented below, the compositions of this invention have very low toxicities, as reflected by their high $LD_{50}$ values. The low toxicity of these complexes is thought to result, in part, from the high stability constant of the complexes. The aminoalkyl moieties provide additional sites for the formation of coordination bonds with the paramagnetic metal ion, thus strengthening the coordination complex. Therefore, the aminoalkyl groups not only neutralize the free carboxylic acid groups of the complexing agent, but they also participate in the formation of the complexes.

The diagnostic compositions of this invention are used in the conventional manner. The compositions may be administered to a warm-blooded animal either systemically or locally to the organ or tissue to be imaged, and the animal then subjected to the NMR imaging procedure. The compositions have been found to enhance the magnetic resonance images obtained by these procedures. In addition to their utility in magnetic resonance imaging procedures, the complexing agents of this invention may also be employed for delivery of radiopharmaceuticals or heavy metals for x-ray contrast into the body.

The invention is further illustrated by the following examples, which are not intended to be limiting.

Example 1

Preparation of a DTPA-Morpholinoethylamide Gd Complex

A DTPA morpholinoethylamide Gd complex was prepared in two steps as shown below:

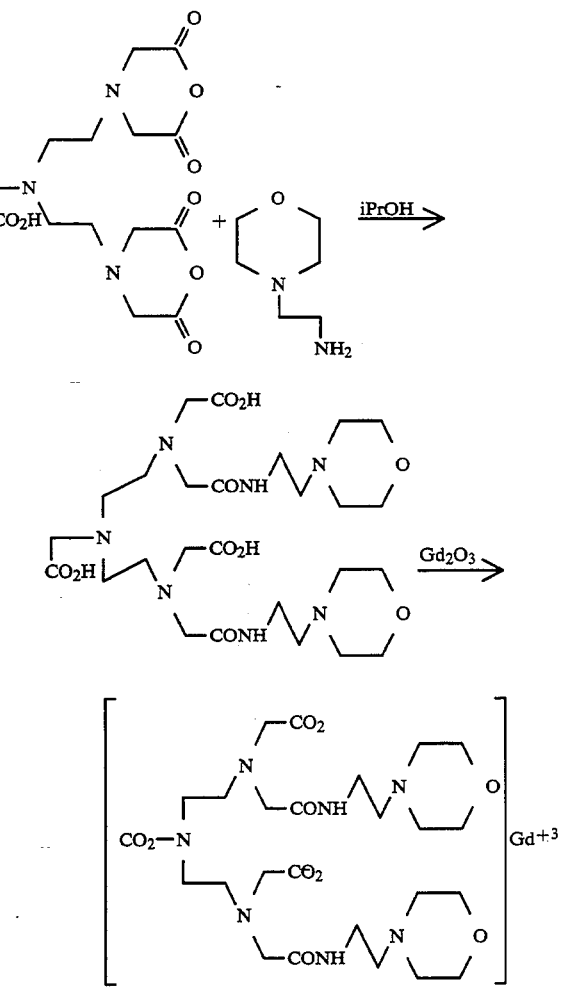

The preparation of [N,N''-bis[N-2((4-morpholino)-ethyl)carbamoyl] diethylenetriamine-N,N',N''-triacetic acid specifically was carried out by the following steps:

A mixture of DTPA-dianhydride (36 g) and aminoethyl-morpholine (27 g) in isopropanol (250 mL) was stirred at ambient temperature for 16 hours. The orange solution was filtered through a fine porosity sintered glass funnel to remove undissolved impurities. The clear filtrate was poured onto ether (2L) and the mixture stirred vigorously for 1 hour. The granular precipitate was collected by filtration, washed with ether (3×1L), and dried. The pale tan solid thus obtained was sufficiently pure for the next step. Yield 60 g (85%). Anal. Calcd. for $C_{26}H_{47}N_7O_{10} \times 0.3H_2O$: C, 50.13; H, 7.64; N, 15.74. Found: C, 50.46; H, 7.80; N, 15.69. The preparation of [N,N''-bis[N-2((4-morpholino)ethyl)-carbamoylmethyl]diethylene triamine-N,N',N''-triaceto]-gadolinium(III) monohydrate was carried out as follows:

A mixture of the ligand (13.8 g) and gadolinium oxide (3.6 g) in deionized water (70 mL) was heated at 65°–70° C. (water bath) for 4 hours and stirred at ambient temperature for 16 hours. The orange solution was then filtered through a fine porosity sintered glass funnel to remove undissolved impurities. The clear filtrate was then poured onto acetone (2L) and the mixture stirred vigorously for 30 minutes. Acetone was decanted off and the gummy-residue was further treated with acetone (1L). The gum began to solidify and after 4 hours, the precipitate was collected by filtration, washed well with acetone (3×1L), dried, and recrystallized from methanol/tetrahydrofuran to afford the complex. Yield, 10 g. (59%). Anal. Calcd. for $C_{26}H_{44}H_7O_{10}Gd \times 1\ H_2O$: C, 39.54; H, 5.83; N, 12.42; Gd, 19.89. Found: C, 39.51; H, 5.76; N, 12.47; Gd. 19.79.

Example 2

Preparation of 1,17-Bis (N,N-dimethyl)-4,14-dioxo-3,6,9,12,15-pentaaza-6,9,12-tris(carboxyethyl)heptadecane (1)

A stirred suspension of DTPA-dianhydride (7.0 g., 19.6 mmol) in isopropanol (35 mL) was treated with N,N-dimethylethylenediamine (3.8 g, 43.1 mmol). The entire mixture was stirred at ambient temperature for about 18 hours. The reaction mixture was filtered to remove insoluble impurities. The clear filtrate was poured into anhydrous ether (2L) and the mixture stirred vigorously for 1 hour. The fine solid was collected by filtration, washed with ether (3×200 mL), and dried at 50° C. to constant weight to yield a colorless solid, 9.0 g (82.0%).

Anal. Calcd. for $C_{22}H_{43}N_7O_8 \cdot 0.5H_2O$ (MW 542.63); C,48.71%; H,8.12%; N,18.08%. Found: C,48.50%; H,8.4%; N,18.09%.

Example 3

Preparation of {N,N''-Bis[N-2((dimethylamino)ethyl)carbamoylmethyl]-diethylenetriamine-N,N'N''-triaceto}gadolinium(III)

A mixture of the ligand (11.50 g, 0.021 mol) and Gd₂O₃ (3.62 g., 0.01 mol) in deionized water (50 mL) was heated. After the reaction was over, the filtrate was poured into acetone (1L). The solvent was decanted off and the residue was further treated with fresh acetone (1L). The precipitate was collected by filtration and it was recrystallized from tetrahydrofuran/methanol to yield the complex as a colorless solid, 3.8 g (30.0%).

Anal. Calcd. for $C_{22}H_{40}N_7O_8Gd \cdot 0.5H_2O$ (MW 697.87): C,38.21%; H,5.79%; N,14.18%; Gd.22.72%. Found: C,38.54%; H,6.19%; N,13.99%; Gd,21.79%.

Example 4

Preparation of 1,17-Bis(4-thiomorpholino)-4,14,dioxo-3.6.9,12,15-pentaaza-6,9,12-tris(carboxymethyl)heptadecane (4)

A stirred suspension of DTPA-dianhydride (7.14 g, 0.02 mol) in isopropanol (50 mL) was treated with freshly distilled aminoethylthiomorpholine (6.3 g, 0.044 mol). The entire mixture was stirred at ambient temperature for about 16 hours. The reaction mixture was filtered to remove insoluble impurities. The clear filtrate was taken to dryness. The gummy residue was purified by flash chromatography over reverse phase (C-18) column. This material was used as such for metal complexation.

Example 5

Preparation of {N,N''-Bis[N-2((4-thiomorpholino)ethyl)carbamoylmethyl]-diethylenetriamine-N,N',N''-triaceto}gadolinium-(III)

A mixture of the ligand (7.0 g, 10.8 mmol) and Gd₂O₃ (1.86 g, 5.1 mmol) in deionized water (35 mL) was heated at 67°–70° C. for 18 hours. After the reaction was over, the filtrate was poured into acetone (2L) and the mixture stirred vigorously for 30 minutes. After 1 hour, acetone was decanted off and the gummy residue was further treated with acetone (1L). The precipitate was collected, washed with acetone and recrystallized twice from acetone/water to give 4.5 g of colorless solid.

Anal. Calcd. for $C_{26}H_{44}N_7O_8S_2Gd \times 1.5H_2O$: C,37.54; H,5.66; N,11.79; S,7.70; Gd.18.89. Found: C,37.80; H,5.51; N,11.90; S,7.52; Gd,19.92

Example 6

Toxicity determination of DTPA-morpholinoethylamide Gd complex

The acute intravenous toxicity of the compound of Example 1 was determined as follows: ICR mice, at 1 to 4 per dose level, received single intravenous injections of the test substance via a lateral tail vein at the rate of approximately 1 ml/minute. The test substances were at concentrations chosen to result in dose volumes of 5 to 75 ml/kg body weight. Dosing began at a volume of 10 ml/kg. Dose adjustments up or down were made to closely bracket the estimated $LD_{50}$ with 4 animals per group (2 males and 2 females). Observations of the mice were recorded at times 0, 0.5, 1, 2, 4 and 24 hours and once daily thereafter for up to 7 days post injection. On the 7th day post injection, the mice were euthanized, weighed and necropsied. Abnormal tissues were noted. At this time a decision was made as to whether any histopathology was to be performed and whether or not the tissues should be retained. Necropsies were also performed on mice expiring after 24 hours post-injection, except for dead mice found on the weekends. The $LD_{50}$ values, along with 95% CI were calculated using a modified Behrens-Reed-Meunch method. The results for the complex of Example 1 are reported below:

$LD_{50}$: 10.0 mmol/kg (no excess ligand, 0.5M solution)

$LD_{50}$: 17.3 mmol/1 kg (5% excess ligand as calcium salt, 0.5M solution)

Example 7

$T_1$-Relativity Determinations $T_1$ or longitudinal relaxation times were measured at 90 MHz for the complex in 25% $D_2O/75\%H_2O$ mixture at 20 mM down to 0.65 mM. The $T_1$ is obtained using the spin-echo sequence on the JEOL FX90Q FT-NMR spectrometer. The relaxivities were determined by applying linear least-squares fit to the $1/T_1$ versus concentration data. The target correlation coefficient ($r^2$) is about 0.9990.

All $^{13}C$ NMR spectra were taken on a JEOL FX9OQQ FT-NMR Spectrometer and all $^1H$ NMR Spectra were taken on a Varian Gemini 300 FT-NMR Spectrometer at room temperature. The IR spectrum was done on a Perkin-Elmer IR Spectrophotometer 727. Elemental analyses were performed by Galbraith Laboratories of Knoxville, Tenn., and Atlantic Microlab of Norcros, Ga. pH measurements were made on a Corning Ion Analyzer 250 meter using a Corning combination electrode. All spectrophotometric measurements were made on a Varian CARY 2215 uv/vis spectrophotometer at room temperature. All computer calculations were done on an IBM Personal System 2 or an IBM-compatible PC Kaypro.

The relaxation rate for the complex of Example 1 was $5.13 \pm 0.07$ mM$^{-1}$sec$^{-1}$ at 90 MHz and 25° C. The correlation coefficient (r$^2$) was 0.9993.

Example 8

Preparation of 1-[N-(2-methoxy)ethyl-N-methyl ]carbamoylmethyl-4,7,10-tris(carboxymethyl)-1,4,7,10-tetrazacyclododecane The title ligand is synthesized from DOTA and CH$_3$OCH$_2$CH$_2$NHCH$_3$ by following the general method reported by Krejearek and Tucker (*Biochem. Biophys, Res. Commun.* 77 581 (1977)).

Example 9

Preparation of Gadolinium (III) 1-[N-(2-methoxy)ethyl-N-methyl] carbamoylmethyl-4,7,10-tris(carboxymethyl)-1,4,7,10-tetraazacyclododecane A mixture of the ligand from Example 8 (10 gr. 0.021 mol. and Gd$_2$O$_3$ (3.6 gr, 0.01 mol) in deionized water (50 ml) is heated at 100° C. until most of the solid is dissolved. The mixture is cooled and filtered through a 0.2 micron filter to remove insolubles present. The filtrate is passed through an ion exchange column and the fractions containing the product are concentrated. The product may be further purified, if necessary, in accordance with conventional procedures. The procedure produces the title compound in good yield.

Example 10

Preparation of 1-[N-2-(4-morpholino)ethyl]carbamolymethyl 4,7,10-tris(carboxymethyl)-1,4,7,10-tetraazacyclododecane The title ligand is synthesized from DOTA and 4-(2-aminoethyl)morpholine by following the method reported by Krejearek and Tucker (*Biochem. Biophys. Res. Commun.* 77 581 (1977).

Example 11

Preparation of Gadolinium (III) 1(-[N-2-(morpholino)ethyl carbamoylmethyl 4,7,10-tris(carboxymethyl)-1,4,7,10-tetrazacyclododecane The procedure of Example 9 is repeated in all essential details except that the ligand used here is the mono 4-morpholinoethylamide of DOTA, synthesized in Example 10. The procedure produces the title compound in good yield.

We claim:

1. A complex having the following formula:

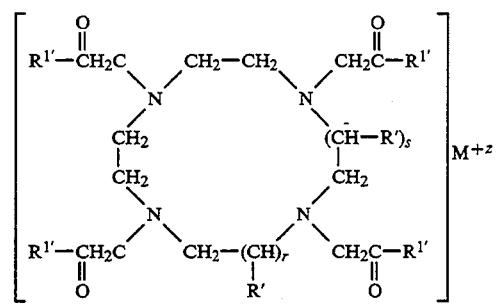

wherein M$^{+z}$ is a paramagnetic ion of an element with an atomic number of 21–29, 42–44 or 58–70, and a valence Z of +2 or +3, r and s are integers between 1 and 6 and can be the same or different, the R' groups can be the same or different and are selected from the group consisting of hydrogen, alkyl having from 1 to 6 carbon atoms and mono or polyhydroxyalkyl, the alkyl portion having from 1 to 6 carbon atoms, the R$^{1'}$ groups can be the same or different and wherein at least one R$^{1'}$ is an aminoalkylamide, R$^{1'}$ selected from the group consisting of —O$^-$ and

wherein R$^{2'}$ is selected from the group consisting of (CH$_2$CH$_2$O)$_p$—R$^{3'}$ and

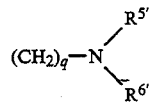

and R$^{4'}$ is selected from the group consisting of H, R$^{2'}$ and R$^{3'}$, wherein R$^{3'}$, R$^{5'}$ and R$^{6'}$ can be the same or different and are selected from the group consisting of hydrogen, alkyl, hydroxy, alkoxy, mono- or poly-hydroxyalkyl, alkoxyalkyl, aminoalkyl or acylamino-alkyl, wherein the carbon-containing portions contain from 1 to about 6 carbon atoms or R$^{5'}$ and R$^{6'}$ can, together with the adjacent nitrogen, form a heterocyclic ring of five, six or seven members wherein 0 to 1 members other than the nitrogen are —O—, —S—,

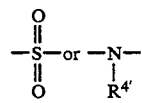

and which members are unsubstituted or substituted by hydroxy, alkyl, aryl, hydroxyalkyl, aminoalkyl, aminoaryl, alkylamino, or carbamoyl wherein the substituents contain from 1 to about 6 carbon atoms, p and q can be the same or different and represent integers between 1 and 6, and wherein z of the R$^{1'}$ groups are —O$^-$ and the remainder of the R$^1$ groups are

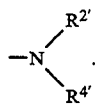

2. The complex of claim 1, wherein $R^{2'}$ is $(CH_2CH_2O)_p$—$R^{3'}$.

3. The complex of claim 1, wherein $R^{2'}$ is

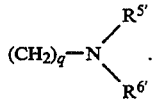

4. The complex of claim 2 or 3, wherein each R' group is hydrogen or alkyl having from 1 to 6 carbon atoms.

5. The complex of claim 3, wherein $M^{+z}$ is chromium (III), manganese (II), manganese (III), cobalt (II), nickel (II), copper (II), praseodymium (III), neodymium (III), samarium (III), ytterbium (III), gadolinium (III), terbium (III), dysprosium (III), holmium (III), or erbium (III).

6. The complex of claim 4, wherein $M^{+z}$ is gadolinium (III), terbium (III), dysprosium (III), holmium (III) or erbium (III).

7. The complex of claim 3, wherein R' is hydrogen, $R^{2'}$ is

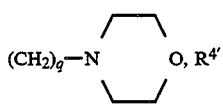

is hydrogen and r and s are each 1.

8. The complex of claim 3, wherein R' is hydrogen, $R^{2'}$ is $(CH_2CH_2O)_p$—$CH_3$, $R^{4'}$ is hydrogen or alkyl having from 1 to 6 carbon atoms and r and s are each 1.

9. A diagnostic composition suitable for enteral or parenteral administration to a warm-blooded animal which comprises an NMR imaging-effective amount of a complex of a paragnetic ion having the following formula:

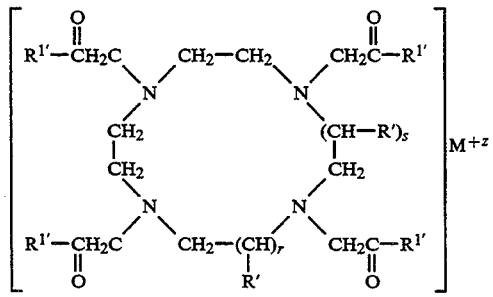

wherein $M^{+z}$ is a paramagnetic ion of an element with an atomic number of 21–29, 42–44 or 58–70, and a valence Z of +2 or +3, r and s are integers between 1 and 6 and can be the same or different, the R' groups can be the same or different and are selected from the group consisting of hydrogen, alkyl having from 1 to 6 carbon atoms and mono or polyhydroxyalkyl, the alkyl portion having from 1 to 6 carbon atoms, the $R^{1'}$ groups can be the same or different and wherein at least one $R^{1'}$ is an aminoalkylamide, $R^{1'}$ selected from the group consisting of —O⁻ and

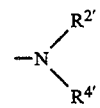

wherein $R^{2'}$ is selected from the group consisting of $(CH_2CH_2O)_p$— $R^3$ and

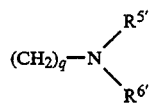

and $R^{4'}$ is selected from the group consisting of H, $R^{2'}$ and $R^{3'}$, wherein $R^{3'}$, $R^{5'}$ and $R^{6'}$ can be the same or different and are selected from the group consisting of hydrogen, alkyl, hydroxy, alkoxy, mono- or polyhydroxyalkyl, alkoxyalkyl, aminoalkyl or acylaminoalkyl, wherein the carbon-containing portions contain from 1 to about 6 carbon atoms or $R^{5'}$ and $R^{6'}$, together with the adjacent nitrogen, can form a heterocyclic ring of five, six or seven members wherein 0 to 1 members other than the nitrogen are

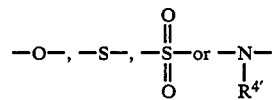

and which members are unsubstituted or substituted by hydroxy, alkyl, aryl, hydroxyalkyl, aminoalkyl, aminoaryl, alkylamino, or carbamoyl wherein the substituents contain from 1 to about 6 carbon atoms, p and q can be the same or different and represent integers between 1 and 6, and wherein z of the $R^{1'}$ groups are —O⁻ and the remainder of the $R^{1'}$ groups are

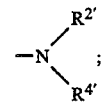

and a pharmaceutically acceptable carrier.

10. The composition of claim 9, wherein $R^{2'}$ is $(CH_2CH_2O)_p$—$R^{3'}$.

11. The composition of claim 10, wherein $R^{2'}$ is

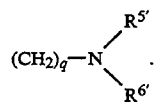

12. The composition of claim 10 or 11, wherein each R' group is hydrogen or alkyl having from 1 to 6 carbon atoms.

13. The composition of claim 9, wherein $M^{+z}$ is chromium (III), manganese (II), manganese (III), cobalt (II), nickel (II), copper (II), praseodymium (III), neodymium (III), samarium (III), ytterbium (III), gadolinium (III), terbium (III), dysprosium (III), holmium (III), or erbium (III).

14. The composition of claim 13, wherein $M^{+z}$ is gadolinium (III), terbium (III), dysprosium (III), holmium (III) or erbium (III).

15. The composition of claim 9, wherein $R^{2'}$ is

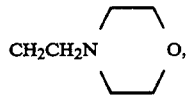

$R'$ is hydrogen, $R^{4'}$ is hydrogen, r and s are each 1 and $M^{+z}$ is gadolinium (III).

16. The composition of claim 10, wherein $R^{2'}$ is $CH_2CH_2OCH_3$, $R'$ is hydrogen, $R^{4'}$ is methyl, r and s are each 1 and $M^{+z}$ is gadolinium (III).

17. The composition of claim 9, which further contains a pharmaceutically acceptable buffer.

18. The composition of claim 17, which further contains a pharmaceutically acceptable electrolyte.

19. The composition of claim 9, which further comprises a complexing agent of the formula

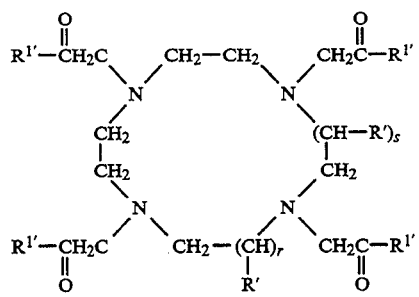

wherein $R'$ and $R^{1'}$ are as defined as in claim 9 and said complexing agent is complexed with one or more physiologically acceptable, non-toxic cations.

20. The composition of claim 19, wherein said complexing agent is employed in an amount ranging from about 0.1 to about 15 mole % of the paramagnetic ion-containing complex and is complexed with one or more cations selected from the group consisting of sodium ions, calcium ions, magnesium ions, copper ions, zinc ions and mixtures thereof.

21. The composition of claim 20, wherein said complexing agent is complexed with calcium ions.

22. A method of performing an NMR diagnostic procedure, which comprises administering to a warm-blooded animal an effective amount of a complex of the formula:

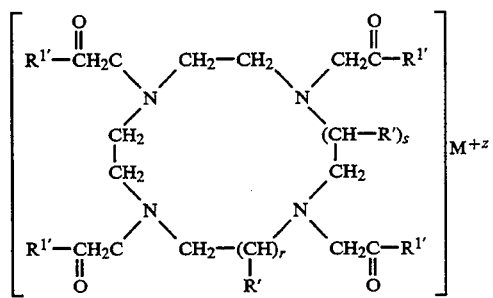

wherein $M^{+z}$ is a paramagnetic ion of an element with an atomic number of 21-29, 42-44 or 58-70, and a valence Z of +2 or +3, r and s are integers between 1 and 6 and can be the same or different, the $R'$ groups can be the same or different and are selected from the group consisting of hydrogen, alkyl having from 1 to 6 carbon atoms and mono or polyhydroxyalkyl, the alkyl portion having from 1 to 6 carbon atoms, the $R^{1'}$ groups can be the same or different and wherein at least one $R^{1'}$ is an aminoalkylamide, $R^{1'}$ selected from the group consisting of $-O^-$ and

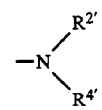

wherein $R^2$ is selected from the group consisting of $(CH_2CH_2O)_p-R^{3'}$ and

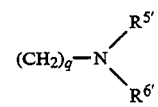

and $R^{4'}$ is selected from the group consisting of H, $R^{2'}$ and $R^{3'}$, wherein $R^{3'}$, $R^{5'}$ and $R^{6'}$ can be the same or different and are selected from the group consisting of hydrogen, alkyl, hydroxy, alkoxy, mono- or poly-hydroxyalkyl, alkoxyalkyl, aminoalkyl or acylamino-alkyl, wherein the carbon-containing portions contain from 1 to about 6 carbon atoms or $R^{5'}$ and $R^{6'}$ can, together with the adjacent nitrogen, form a heterocyclic ring of five, six or seven members wherein 0 to 1 members other than the nitrogen are

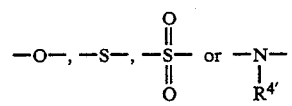

and which members are unsubstituted or substituted by hydroxy, alkyl, aryl, hydroxyalkyl, aminoalkyl, aminoaryl, alkylamino, or carbamoyl wherein the substituents contain from 1 to about 6 carbon atoms, p and q can be the same or different and represent integers between 1 and 6, and wherein z of the $R^{1'}$ groups are $-O^-$ and the remainder of the $R^{1'}$ groups are

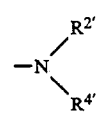

and then exposing the animal to an NMR procedure, thereby imaging at least a portion of the body of the warm-blooded animal.

23. The method of claim 22, wherein $R^{2'}$ is $(CH_2CH_2O)_p-R^{3'}$.

24. The method of claim 22, wherein $R^{2'}$ is

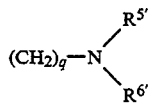

25. The method of claim 22, wherein $M^{+z}$ is chromium (III), manganese (II), manganese (III), cobalt (II), nickel (II), copper (II), praseodymium (III), neodymium (III), samarium (III), ytterbium (III), gadolinium (III), terbium (III), dysprosium (III), holmium (III), or erbium (III).

26. The complex of claim 25, wherein $M^{+z}$ is gadolinium (III), terbium (III), dysprosium (III), holmium (III) or erbium (III).

27. The method of claim 22, wherein the pharmaceutically acceptable carrier contains a pharmaceutically acceptable buffer.

28. The method of claim 27, wherein the pharmaceutically acceptable carrier contains a pharmaceutically acceptable electrolyte.

29. The method of claim 22, wherein the pharmaceutically acceptable carrier contains a complexing agent of the formula

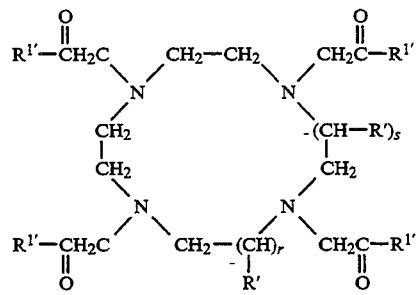

wherein R' and $R^{1'}$ are as defined as in claim 22 and said complexing agent is complexed with one or more physiologically acceptable, non-toxic cations.

30. The method of claim 29, wherein said complexing agent is employed in an amount ranging from about 0.1 to about 15 mole % of the paramagnetic ion-containing complex and is complexed with one or more cations selected from the group consisting of sodium ions, calcium ions, magnesium ions, copper ions and zinc ions and mixtures thereof.

31. The method of claim 30, wherein said complexing agent is complexed with calcium ions.

* * * * *

UNITED STATES PATENT AND TRADEMARK OFFICE
CERTIFICATE OF CORRECTION

PATENT NO. : 5,376,358
DATED : December 27, 1994
INVENTOR(S) : R. Rajagopalan, et al It is certified that error appears in the above-indentified patent and that said Letters Patent is hereby corrected as shown below:

On the title page, item [75] Inventors: "Rajagopolan" should be -- Rajagopalan--.

item [56], under OTHER PUBLICATIONS: insert the following:
Organic Chemistry, 2nd Ed., (1980), p. 810; Chemical Abstracts, Vol. 83, 10186-87 (1975); Chemical Abstracts, Vol. 70, 87783z (1969);

Column 5, line 3, "The" (first occurrence) should read --the--.

Signed and Sealed this

Ninth Day of January, 1996

Attest:

BRUCE LEHMAN

*Attesting Officer*     *Commissioner of Patents and Trademarks*